United States Patent [19]

Silvian

[11] Patent Number: 4,681,111
[45] Date of Patent: Jul. 21, 1987

[54] ANALOG AND DIGITAL TELEMETRY SYSTEM FOR AN IMPLANTABLE DEVICE

[75] Inventor: Sergiu Silvian, Pasadena, Calif.

[73] Assignee: Siemens-Pacesetter, Inc., Sylmar, Calif.

[21] Appl. No.: 720,556

[22] Filed: Apr. 5, 1985

[30] Foreign Application Priority Data

Mar. 27, 1986 [WO] PCT. Int'l Appl. .................. PCT/US86/00645

[51] Int. Cl.[4] .............................................. A61B 5/00
[52] U.S. Cl. .............................. 128/419 PT; 128/697; 128/903
[58] Field of Search .................. 128/419 PG, 419 PT, 128/630–631, 697, 903; 332/22

[56] References Cited

U.S. PATENT DOCUMENTS

| | | | |
|---|---|---|---|
| 3,534,728 | 10/1970 | Barrews | 128/631 |
| 4,026,305 | 5/1977 | Brownlee et al. | 128/903 |
| 4,220,156 | 9/1980 | Schulman et al. | 128/903 |
| 4,223,679 | 9/1980 | Schulman | 128/419 PT |
| 4,281,664 | 8/1981 | Duggan | 128/903 |
| 4,361,153 | 11/1982 | Slocum et al. | 128/419 PT |
| 4,494,545 | 1/1985 | Slocum et al. | 128/419 PT |
| 4,532,932 | 8/1985 | Batty, Jr. | 128/631 |
| 4,556,063 | 12/1985 | Thompson et al. | 128/903 |
| 4,558,284 | 12/1985 | Zaidenweber | 329/126 |
| 4,593,284 | 6/1986 | Clifford et al. | 340/870.18 |

OTHER PUBLICATIONS

Benelli et al., "I.E.E.E. Journal on Selected Preas. in Communications", vol. SAC2, No. 1, Jan., 1984, pp. 77–80.
Lindsey et al., "Telecommunications Systems Engineering", Prentice-Hall, 1973, p. 11.

Primary Examiner—William E. Kamm
Attorney, Agent, or Firm—Robert R. Meads; Bryant R. Gold; Leslie S. Miller

[57] ABSTRACT

In an implantable device, transmission and reception of digital information is accomplished as well as the transmission and reception of analog information. The analog signal is FM modulated for transmission and the digital signal is phase modulated for transmission. The FM modulated signal is used as a clock in the phase encoding of the digital signal and thus provides a signal simultaneously carrying analog and digital information. Means for reception of the analog and digital information is taught. The use of PSK (phase shift keying) as the phase modulation scheme for transmission and reception is also taught.

10 Claims, 17 Drawing Figures

ANALOG AND DIGITAL TELEMETRY SYSTEM FOR AN IMPLANTABLE DEVICE

BACKGROUND OF THE INVENTION

This invention relates to a telemetry system for implantable devices. Such devices are used for a wide range of purposes within the body. The most commonly known of such devices is the cardiac pacemaker. Other well-known devices are for stimulation or sensing, or both, with respect to the brain, spinal cord, muscles, bones, nerves, glands or other body organs or tissue.

Implantable devices are becoming more and more complex and commonly include sophisticated data processing hardware such as microprocessors, or devices akin to microprocessors, ROM and RAM memories, LSI (large scale integration) devices as well as other computer hardware and related techniques. Information transmitted to and from the implanted device comprises device identification, biological data, parameters of present operation of the device (from previous settings), technical information concerning proper functioning of the device, battery condition, patient and physician data, up-to-date programming information for the device and verification of information transmitted to and from the device.

With more and more data being processed and available within the implantable device, there is a need to transmit more and more data from the implanted device to external devices, for analysis, reprogramming of the implantable device or other purposes. The need is for data to be transmitted in both directions in a reasonable amount of time.

There are, of course, limitations surrounding the design of new implantable systems of portions thereof. One of the most limiting aspects is the conservation of energy. An implanted device is customarily powered by a long-lasting internal battery and so the current consumption of a telemetry system becomes one of the most important of factors to be considered in the design of such a system. It is now possible to include A to D converters (having low energy consumption) in implantable devices inasmuch as they can now readily be incorporated in LSI circuits. Such converters draw little current while converting analog signals to digital signals.

Prior art devices have utilized various methods of communicating non-invasively through the skin. U.S. Pat. No. 4,223,679 entitled Telemetry Means for Tissue Stimulator System, issued Sept. 23, 1980 shows a device which uses little or no current to transmit information, relying on reflected impedance of an internal L-R or L-C circuit energized by an inductively coupled, external L-R or L-C circuit. The external circuit may utilize an RF (radio frequency) magnetic field carrier. In the cited patent, a voltage controlled oscillator (VCO), in the implanted device, is controlled by the signal to be telemetered. The VCO, in turn, varies the impedance which is reflected. If the signal controlling the VCO is a binary digital signal (varies, from one value to a single other value) it becomes encoded by the VCO which then varies from one frequency to one other frequency. This technique is known as FSK (frequency shift keying). Each bit duration—the time in which the binary digit (bit) is expressed—requires a number of carrier cycles. Therefore, the bit rate cannot be higher than 10 to 30 per cent of the VCO center frequency. On the other hand, the RF carrier frequency cannot be too high inasmuch the implanted device metal enclosure attenuates as a one-pole low-pass filter having an upper cut-off frequency at 10 to 30 kHz. Also, the external oscillator L-C circuit usually has a Q (quality factor) of 20 to 50, which limits the useful modulation bandwidth to 2 to 5 per cent of the RF carrier frequency. Using FSK encoding, the maximum bit rate is thus limited to 0.2 to 1.5 per cent of the RF carrier frequency. Thus, a 36 kHz carrier frequency could transmit 72 to 540 bits per second. Data rates are commonly on the order of 100 bits per second or less. With thousands and even tens of thousands of bits of data to be transmitted, much higher telemetry speed is needed. The information can then be read out in a fraction of the time formerly required.

Another prior art device is illustrated by U.S. Pat. No. 4,281,664 issued Aug. 4, 1981, for an Implantable Telemetry Transmission System for Analog and Digital Data. The system therein uses a VCO to FM encode the analog and digital data in the same way as the first mentioned patent. It pulses an implanted coil on each positive transition of the VCO. At each pulse, the above coil will generate a damped oscillation whose frequency is determined by a parallel capacitor. At the receiving side, another coil, tuned to the above frequency, receives the damped pulses and receiving circuitry reconstructs the VCO positive-going transitions. Digital data is transmitted by FSK using the VCO in a similar manner as explained therein for analog data. Such scheme has the drawback that the bit rate cannot exceed approximately 1 per cent of the carrier frequency. Inasmuch as the implanted metal enclosure attenuates the high frequency, the carrier frequency cannot be increased above approximately 10 kHz without a corresponding increase in coil driving power, which in turn, will require increased power consumption.

The implanted device tranmitter, in accordance with one emobidment of the present invention, encodes serial data to be transmitted using phase-shift-keying (PSK, or Manchester encoding) on a fixed frequency clock. The resulting signal controls an on/off switch (such as a semiconductor switch) connected across an L-C circuit tuned to the external device RF carrier frequency. The inductor (providing the L) is magnetically coupled to an external inductor (which provides the L in an external L-C circuit.) As the switch in the implanted device is opened and closed in accordance with the data to be transmitted, it causes a variation (modulation) of the reflected impedance which is received by the external L-C circuit. It may be that the switch, which is electronic in nature, exhibits little or no resistance (or impedance) when closed and a greater amount of resistance (or impedance) when in the open condition. The concept is that the impedance, or characteristics of the L-C circuit be varied, in response to the signal to be transitted. In other embodiments, the electrical charge in such circuit may be provided from within the implanted device or, an rf transmitter utilizing the L-C circuit as its antenna may be used to transmit information.

In a first mode of operation, the sytem of the invention permits transmitting digital data without the need of a VCO in the transmitter, if desired, and allows a higher bit rate with minimal hardware implementation. The bit rate can now be 2 to 5 per cent of the RF carrier frequency, or 3.3 to 10 times faster than the system discussed above.

In an alternate embodiment, a second mode is provided in which the implanted system uses analog signals required to be telemetered to modulate a voltage-controlled oscillator (VCO) providing frequency modulated signals which can also be transmitted by the telemetry system.

In another embodiment, a third mode is provided in which the implanted system in the sending of analog signals (which causes frequency modulated signals) inserts from time to time digital signals which may comprise a few bits of digital information or a "marker"

In still another embodiment, a fourth mode is provided wherein, instead of using a fixed frequency clock as the carrier for the PSK transmission of digital data, modulated FM carrier is used as the clock (and carrier) for the digital signals, and thus combines in one channel simultaneous transmission of both analog and digital information.

Figure 13:
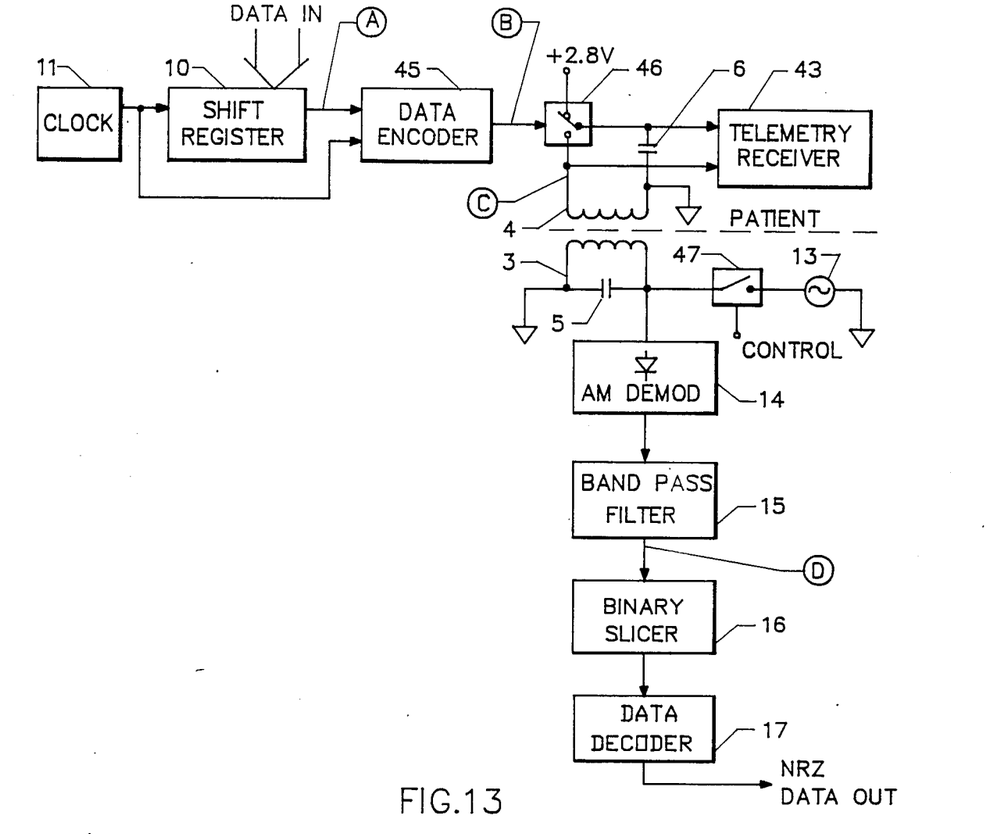
FIG. 13 illustrates a modification of the telemetry system shown in FIG. 1 by utilizing impulse-type coil driving.
Figure 14:
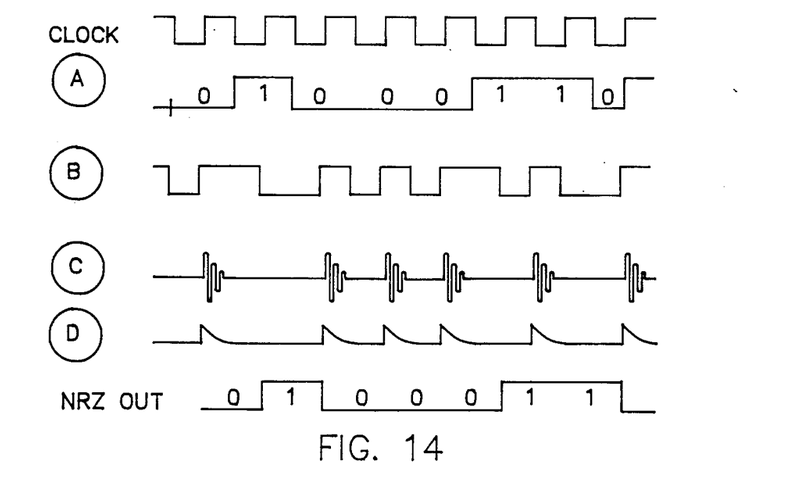
FIG. 14 shows the signals at various locations in the system shown in FIG. 13, when PSK encoding is used.

A further variation to the above embodiments is one in which, in place of the reflected impedance principle, the implanted coil (the coil tuned to a 5 to 50 kHz frequency by a capacitor,) is excited by a series of impulses corresponding to the positive edges of the encoded data, as taught in FIGS. 13 and 14.

The antenna for transmission from the implanted device, at higher frequencies, becomes very short and may, at such high frequencies, provide the necessary inductance and capacitance itself. A tuned stub may be satisfactorily used in some instances. Ferrite beads, ferrite coils, toroids and other high frequency components may be utilized in the transmission and reception portions or in the antennas in order to obtain proper impedances and to match such impedances.

It is possible using the concept of the invention to transmit at frequencies up to, and possibly beyond, 200 MHz. Above such frequencies, the saline solution of the body tissue begins to cause problems such as RF heating, and energy losses, including transmission losses.

Still another variation is one in which an active rf transmitter is used in the implanted device to transmit the information, using the implanted coil as the antenna.

It is intended that all suitable forms of transmission, whether active or passive, be included within the concept of the invention. Thus, reflection of impedance, transponder, rf transmission (or other active transmitter), telemetry, current or voltage variation, ultrasonic, light, infrared, or other suitable method or mode of getting information from one point to another without a direct wire are within the concept of the invention.

Thus, the words "transmission", "obtaining" or "providing" are to be interpreted herein and in the claims as including within their meaning all such methods or modes.

In addition to PSK encoding as explained herein, a number of other pulse encoding schemes may be used, such as FM (frequency modulation—1 pulse for a zero, 2 pulses for a 1), MFM (modified FM—using less than one pulse per bit—known as Miller coding) or MM (modified Miller) as well as various biphase coding schemes. Such encoding schemes are known to those skilled in the encoding art. Any one of such encoding schemes will permit the same increase in data rate as explained in the above PSK encoding as explained in connection with PSK encoding, without extra power to be required. This will become apparent in connection with FIG. 13 and its description.

The signal received b the external L-C circuit is processed and decoded from PSK (or other encoding as previously mentioned) to NRZ data. For the embodiment in which FM modulation (VCO) is used to transmit analog data in addition to digital data, the output for the analog data is taken from an FM demodulator and filter.

Suitable switches in the implantable device provide selection of the available modes. Such switches may, of course, be controlled, or set, by information transmitted from outside the patient's body or from internal control.

A similar transmitter and receiver may be used to transmit information from outside the body to the implanted device. It is most likely that the information transmitted to the implanted device would be digital in nature, however, both analog and digital data could be transmitted in, just as both kinds of data can be transmitted out. Some of the components, viz., the L-C circuits of the outward transmitting system could be shared and used in transmitting information into the implanted device.

DETAILED DESCRIPTION OF THE INVENTION

This invention provides an improved telemetry system for transmitting information between an implanted device and an external receiver. The improvement lies in increasing the rate at which data is transmitted and, thus, increasing the capability of the system.

Figure 1:
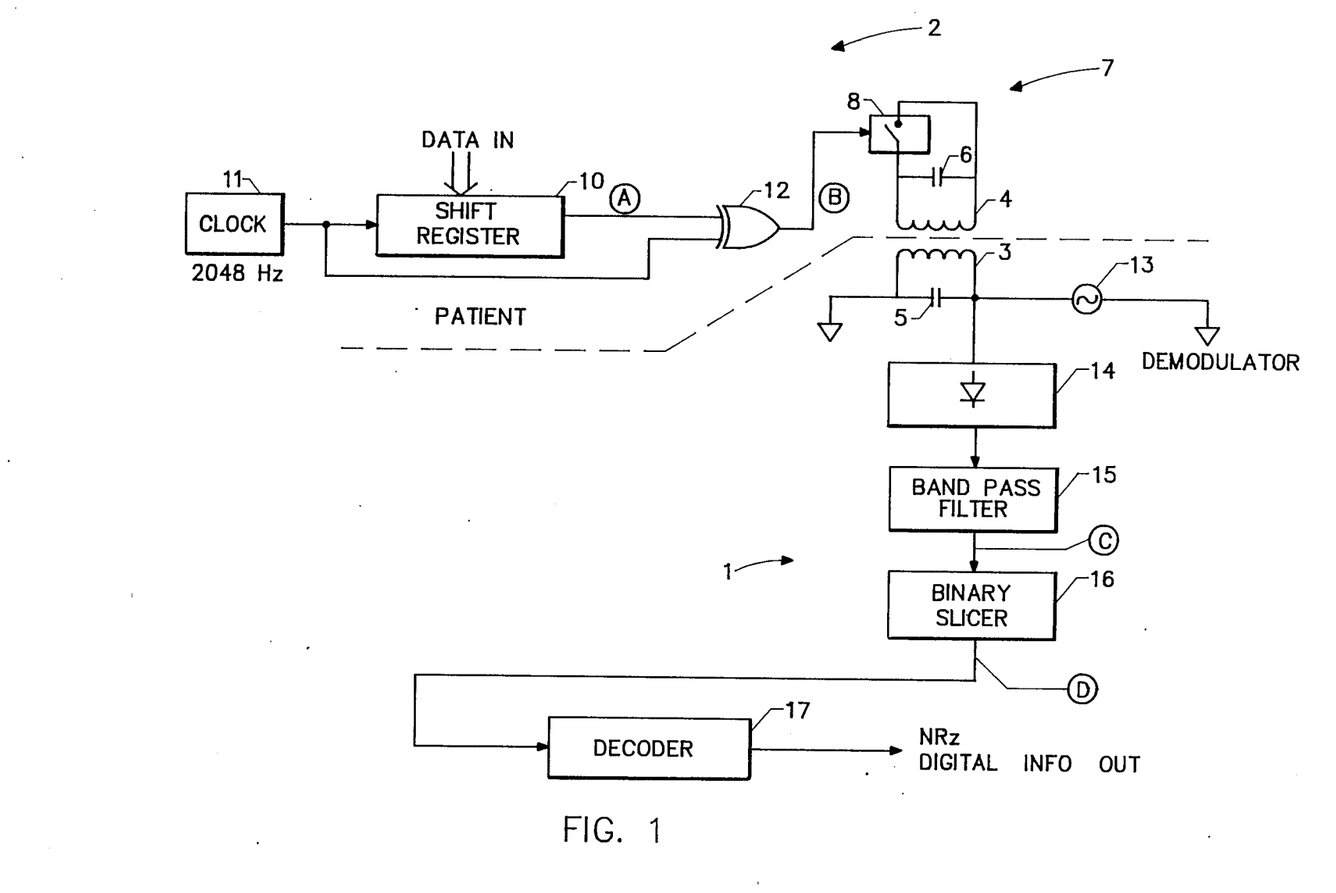
FIG. 1 illustrates the digital device of the invention, showing a telemetry system having greater data transmission rate than prior art systems.

Referring now to FIG. 1, there is shown a receiving, external device 1 and an implanted transmitting device 2. Such devices each have an inductor, 3 and 4, respectively, which are magnetically coupled to each other. Such inductors are each connected with respective capacitances 5 and 6, forming tuned circuits. Tuned circuit 7 (the implanted inductor 4 and capacitor 6) includes a switch 8 which is controlled by the signal placed upon it. It is a low-impedance, semiconductor switch. It is common practice to use CMOS switches in implanted devices. When switch 8 is closed, inductor 4 and capacitor 6 are shorted and the reflected impedance to inductor 3 is less than when switch 8 is open. Information is transmitted by opening and closing electronic switch 8. Switch 8, it may be appreciated, may be a device which provides increased resistance or impedance when open, as distinguished from being an entirely open circuit. When the switch is open, the inductor 4 and capacitor 6 extract a different amount of energy from inductor 3 and capacitor 5 than when the switch 8 is closed. Thus, the reflected impedance changes and thus, the impedance of the external tuned circuit changes. This causes a modulation of the external oscillator. It is pointed out in U.S. Pat. No. 4,223,679 how the system may be operated as an FM/AM system as well as FM/FM system.

As used herein, "telemetry" and, particularly in the claims, "radio frequency transmission" are intended to include within their meaning all wireless communication by electromagnetic energy. Inductive coupling from one coil to another, as well as transmission and reception of radio waves, is intended to be included.

Figure 9:
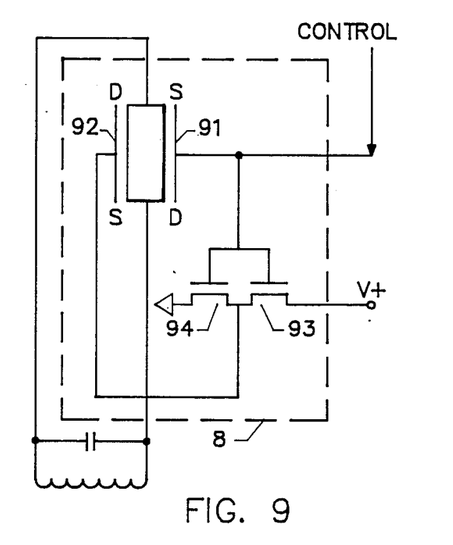
FIG. 9 is an electrical diagram of one example of an electronic switch which may be used in the L-C circuit of the invention.

FIG. 9 is an electrical schematic of a suitable switch 8 for use in the tuned circuit. Two CMOS transistors 91 and 92, having the source of one connected to the drain of the other, are connected in the L-C circuit. The gate of transistor 91 is driven directly by the control signal, and the gate of the transistor 92 is driven by two transistors 93 and 94 (which form an inverter).

Referring again to FIG. 1, digital information obtained from, whatever source provides the digital input to shift register 10. In a particular embodiment, digital data may be sent to the shift register directly from RAM memory or from an A to D converter. The input to the shift register may be serial or parallel. Clock 11, running, in this example, at 2048 Hz, shifts the data through the shift register which provides an output to EXOR (exclusive or) gate 12. Gate 12 also receives the clock signal directly from the clock 11 to provide an output which is a PSK signal. In the embodiment contemplated, when the data is "1", it shifts the phase of the clock signal 180 degrees; and when the data is "0", no phase shift appears.

In simpler terms, the output of the shift register (which contains the data desired to be transmitted) is the modulating signal and the clock signal is the carrier. Starting when the rising edge of a data pulse is provided by shift register 10 (indicating a change from a digital 0 to a digital 1,) the carrier pulse at the output of gate 12 is shifted 180 degrees. The output stays at such phase shift until a falling edge arrives (indicating a change from digital 1 to digital 0) at which point the phase of the output carrier at gate 12 changes back 180 degrees to its original phase. In this manner, a PSK signal is provided. The above discussion assumes, of course, NRZ (non-return to zero) digital encoding at the shift register 10.

Figure 2:
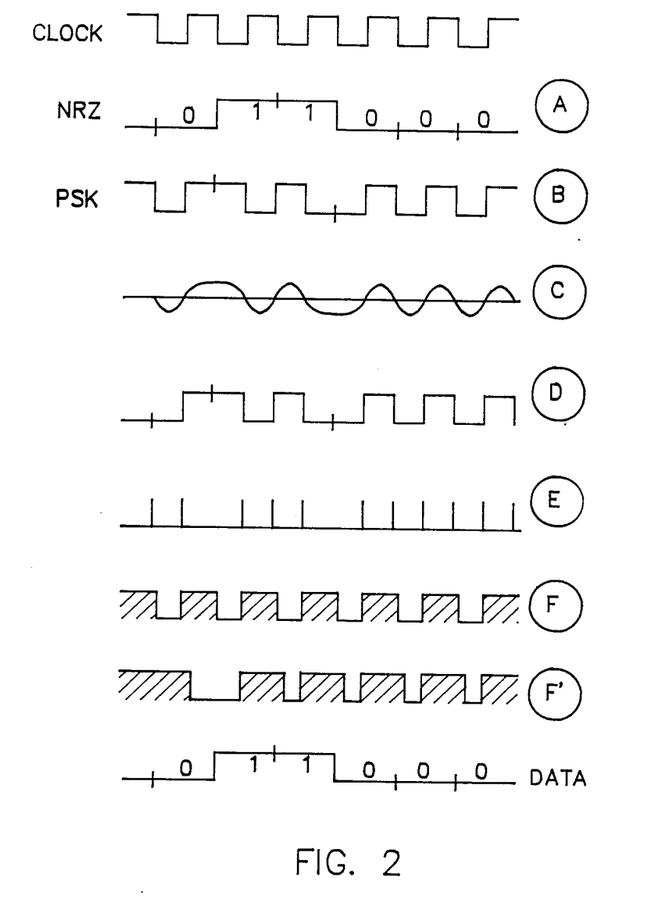
FIG. 2 is a composite of digital signals and waveforms existing at given locations in the digital device of FIG. 1.

Reference to FIG. 2 readily shows this concept. The first line is the clock signal. Line A represents an NRZ encoded signal 011000. The PSK signal, provided at the output of EXOR gate 12 of FIG. 1 is shown on line B. It is noted that upon the appearance of the digital 1, the PSK signal changes phase 180 degrees from the clock signal and stays changed until the next digital 0 appears, at which time the PSK signal reverts back to its original phase, the clock phase.

It should be pointed out that EXOR gate 12 can be removed. By this variation, the transmitter will transmit data as it comes out of the shift register. By doing so, there is a small advantage in that the NRZ frequncy spectrum, usually expressed as "main lobe", is from DC to 1.0 times the bit rate as compared to 0.1 to 1.6 times the bit rate for PSK. On the other hand, this transmission has the important disadvantage that the clock is not transmitted with the data and for long strings of 0's or 1's, the receiver can drop out of synchronization. However, this disadvantage can be partially removed if data is precoded to avoid long strings of 0's or 1's. The data might, of course, also be encoded as pulse width modulation, pulse position modulation, or pulse frequency modulation, of which FSK is one form, in which only two frequencies are used.

Referring again to FIG. 1, the PSK signal drives switch 8 of the tuned circuited comprised of inductor 4 and capacitor 6 and as previously described provides a change in impedance (in accordance with the PSK information) which is sensed (through magnetic induction) by the external tuned circuit, inductor 3 and capacitor 5. The power for this sensing is provided by the external device. Oscillator 13, connected to the tuned circuit, oscillates at a frequency in the RF range as determined primarily by the tuned circuit comprised of inductor 3 and capacitor 5. In order to satisfactorily transfer energy, inductor 4 and capacitor 6 are approximately tuned to that same frequency. Oscillator 13 may be a Colpitts circuit, although most any other oscillator would perform well. This oscillator may, for example, run at 36 kHz. The circuit may be that shown in FIG. 2 of U.S. Pat. No. 4,223,679, referred to previously.

A demodulator 14, which in some cases might be a simple AM detector, a synchronous detector, or, in other cases, an FM demodulator, provides the information to a band pass filter 15 (which pass band might be on the order of 200–2400 HZ). An AM demodulator, as a nonlinear element, mixes any interference signals with the carrier frequency and they must be removed. The band pass filter's main purpose is to filter out the carrier frequency and provide enough attenuation for removing any interfering signals. The band pass filter will pass only those frequencies strictly necessary to reconstruct the transmitted signals. It is especially important to attenuate the second harmonic of a CRT horizontal sweep frequency, which usually is 31.5 kHz. If the carrier frequency is 36 kHz this means the band-pass filter will have to attenuate significantly at 4.5 (36–31.5) kHz.

Figure 10:
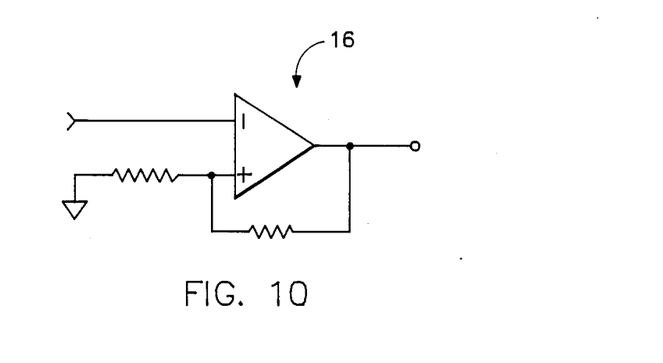
FIG. 10 is a schematic of a bit slicer, or comparator, sometimes called a "comparator with hysteresis."

The band pass filter 15, in turn, provides the signal indicated at C, in FIG. 2, to binary slicer 16 (comparator) which is illustrated in one embodiment in greater detail in FIG. 10. The binary slicer 16, or comparator, is simply an amplifier with feedback. The binary slicer 16 provides at its output the original PSK digital signal indicated at D in FIG. 2. A decoder 17 provides the digital output signal originally held in the shift register 10. In this embodiment, the information is illustrated as being NRZ and the decoder 17 is illustrated as being a PSK decoder. Other coding schemes, may, of course, be utilized.

It should be pointed out that in some situations a frequency divider can be inserted in the clock to the shift register circuit in FIG. 1, such that a bit duration will extend to more than one period of the clock. In this way, various other coding schemes are available.

FIG. 1 represents the first mode of transmission. Such mode is digital in nature.

Figure 3:
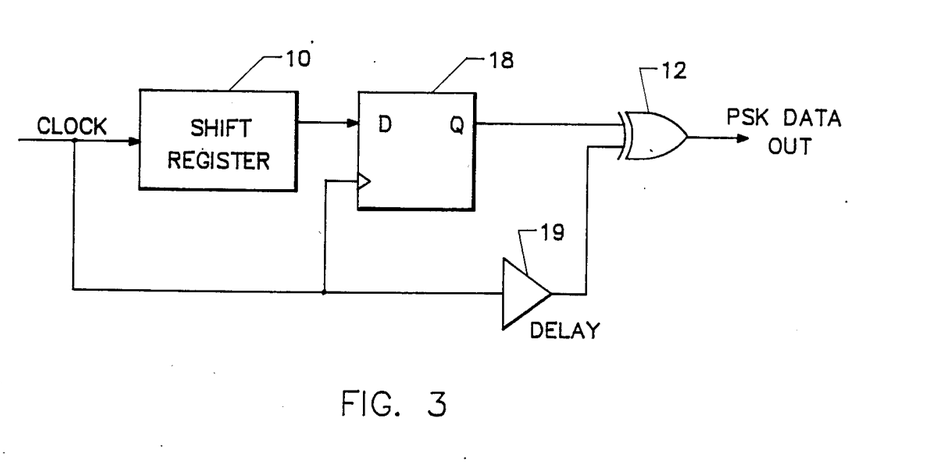
FIG. 3 is an improved phase shift encoding circuit.

It may be appreciated that the EXOR gate 12 of FIG. 1 may at times generate incorrect signals because of the propagation delay in the shift register. For greater accuracy and reliability the embodiment of FIG. 3 may be used to better synchronize the shift register data output to the clock. A type D flip flop 18 holds, successively, each shifted bit output of the shift register and delay (or buffer) 19 is included to match the propagation delay of the flip flop 18.

Figure 4:
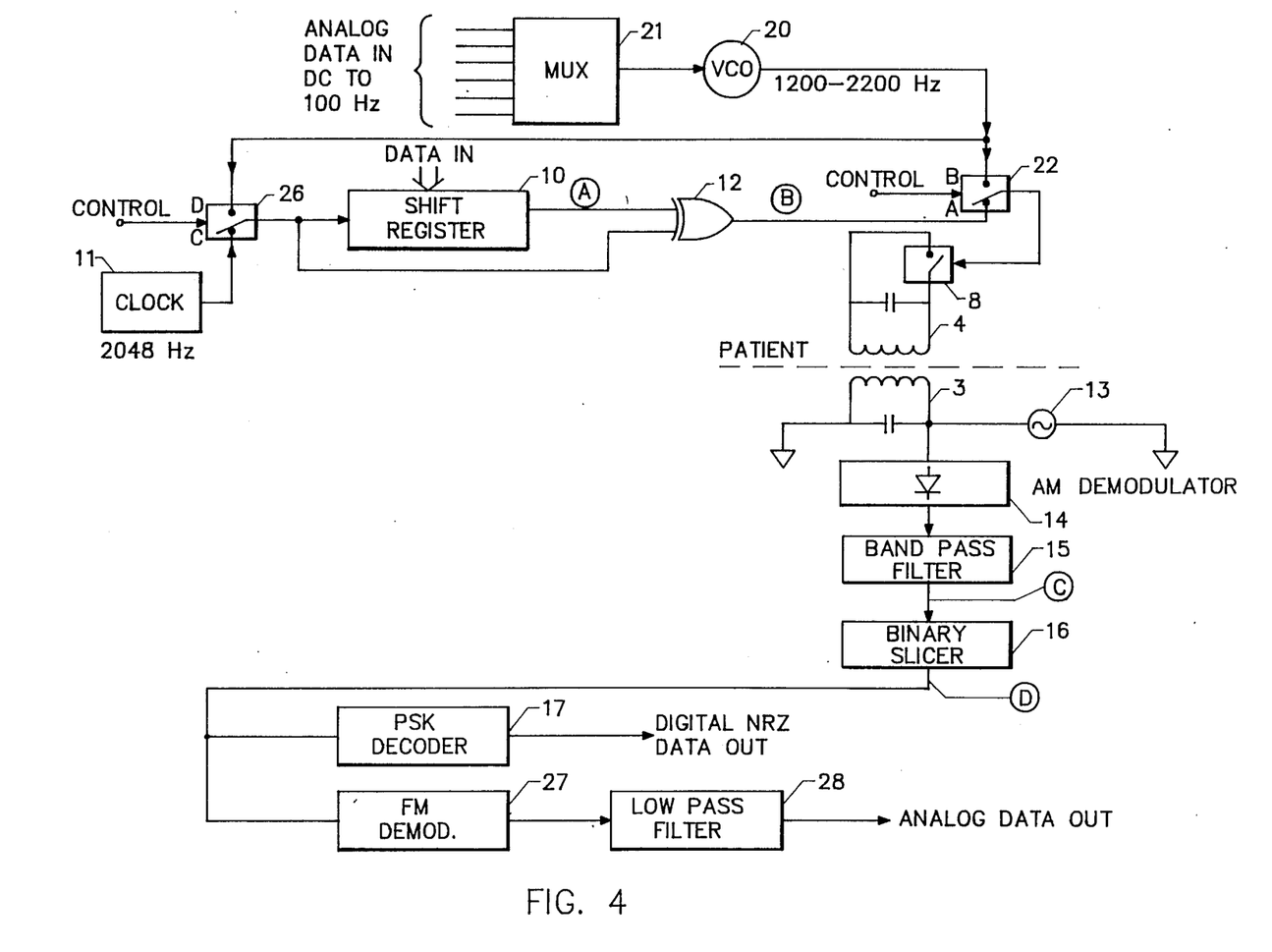
FIG. 4 is an alternate embodiment in which both analog and digital data may be sent.
Figure 5:
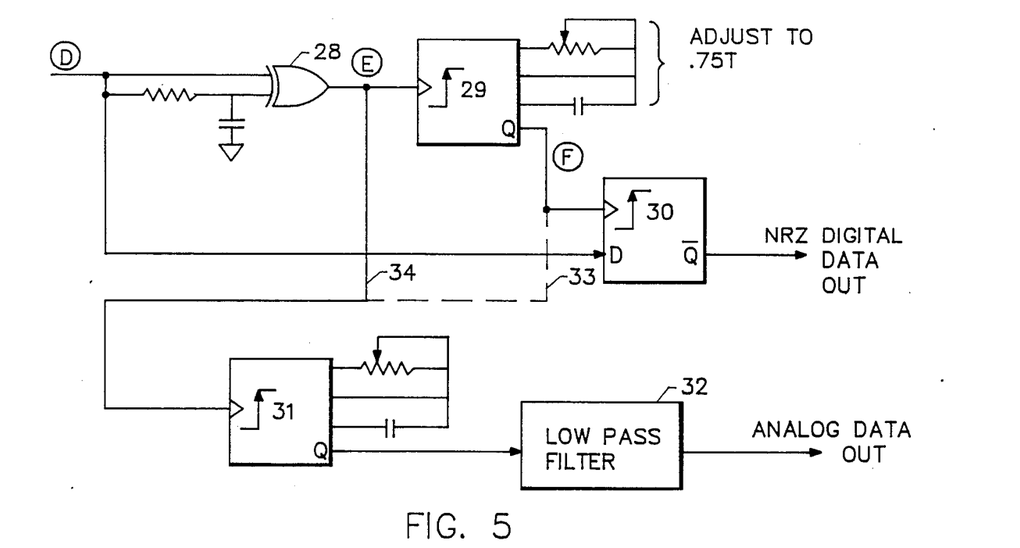
FIG. 5 is an embodiment of the decoding and demodulating portion of the receiver.

The PSK decoder 17 in FIG. 1 or FIG. 4 may be implemented in many ways, depending on the signal-to-noise ratio. At lower values, a more elaborate circuit having a coherent PSK detector and a PLL clock recovery circuit is recommended to be used. At the better signal-to-noise ratios, (15 db or higher) a simple circuit can be used as shown in FIG. 5 in which EXOR gate 28 drives monostable multivibrator 29 which, in turn, regularly clocks flip flop 30 (while it is receiving the digital data) and thus it provides the NRZ digital data output.

The timing diagram of FIG. 2 illustrates a waveform CIRCLE C which exists at the output of the band phase filter 15 in FIG. 1 or FIG. 4. Such waveform is reconstructed by binary slicer 16 (comparator with hysteresis) to be the waveform shown at CIRCLE D in FIG. 2. In FIG. 5, EXOR gate 28 changes such waveform to the pulses shown at CIRCLE E, FIG. 2. Flip flop 29, a non-retriggerable one-shot multivibrator, FIG. 5 creates a new clock signal F, FIG. 2, based on such pulses. Such clock signal F is used by flip flop 30 to decode the CIRCLE D pulses received at the D input to NRZ. The output of flip flop 30 is NRZ digital data. The CIRCLE F' wafeform of FIG. 2 shows how the multivibrator will center itself if wrongly triggered by an interbit transition as can happen when the transmission just starts.

The second mode of transmission, which is analog in nature, is similar to that shown in cited U.S. Pat. No. 4,223,479. This is illustrated in FIG. 4 in which a voltage controlled oscillator 20 (VCO) receives the output of a multiplexer 21 (MUX) whose input is a plurality of channels of analog data. Such data, for example, might be information representing the stimulation pulses as well as the electric potentials in the right or left atrium or in the right or left ventricle, or both, sensed by the implanted device. Such information is the kind of information displayed by an electrocardiogram (ECG of EKG). In a cerebellar device, the information might be that displayed by an electroencephalograph (EEG). The frequencey of the VCO 20, controlled by the input signal, can be modulated from 1200 to 2200 Hz.

Figure 8:
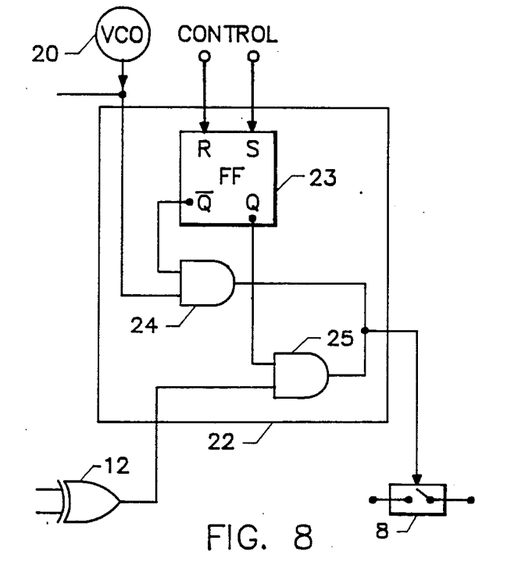
FIG. 8 is an electrical diagram of one example of a mode switch which may be used in the device of the invention.

The control of mode selection switch 22 may be exercised from within the implanted device or controlled by external command. A mode control switch 22 suitable for use is illustrated in FIG. 8, in which an RS flip flop 23 is controlled by the control signal. The output of such flip flop together with AND gates 24 and 25 determine which of the signals from the EXOR gate 12 or the VCO 20 is sent to the tuned circuit switch 8.

Referring again to FIG. 4, the analog information, in this second mode of operation (similar to the case of mode one using digital information) is demodulated in demodulator 14, filtered, and conditioned by binary slicer 16. It is then, however, sent to FM demodulator 27, inasmuch as the VCO provides an FM modulated signal. After passing through low pass filter 28, to remove all frequencies but the range of frequencies being transmitted, an output of analog data is provided. The FM modulated signal may be demodulated using other frequency-to-voltage conversion techniques known in the art.

For example, the decoding of the FM transmission may be that shown in FIG. 5. One-shot multivibrator 31 receives the CIRCLE E pulses (FIG. 2) to provide output signals to low pass filter 32 which in turn provides the analog data output. Dotted line 33 in FIG. 5 is utilized (instead of line 34) if the fourth mode of operation is utilized (in which the modulated VCO signal is the clock signal for the shift register). The fourth mode of operation is discussed below. Filter 32 may be a Bessel low pass filter which is based on the relation between the frequency of CIRCLE E and the duty cycle of the one-shot multivibrator 31. By doubling the incoming frequency (from CIRCLE D TO CIRCLE E), the demodulator is more sensitive as each half-period is taken into account. It is pointed out that any FM demodulator, including a low-pass filter, might be used in order to generate analog data rather than the one-shot and the low pass filter 32, as shown. The filter 32 is necessary to smooth the signal generated by the multivibrator 31.

In review, if switch 22 (FIG. 4) is controlled to be at A, the information being transmitted out is from the shift register and is phase modulated as explained previously, if switch 26 is controlled to be at C. In this mode, the shifting in the shift register is caused by the clock. This is the mode of operation, which is digital in nature, and was previously explained as mode 1.

A third mode of transmission is possible in which switch 22 stays at B for most of the time, (with switch 26 remaining at C) but intermittently thrown to A to transmit a few bits of digital signal which are sent as a "digital marker" or other inserted digital bits in the FM signal. The PSK decoder will recognize the digital marker. The FM demodulator may indicate the digital marker as a "glitch" or spike, or be put on hold during the marker transmission which, ordinarily, would be very short in duration.

Figure 6:
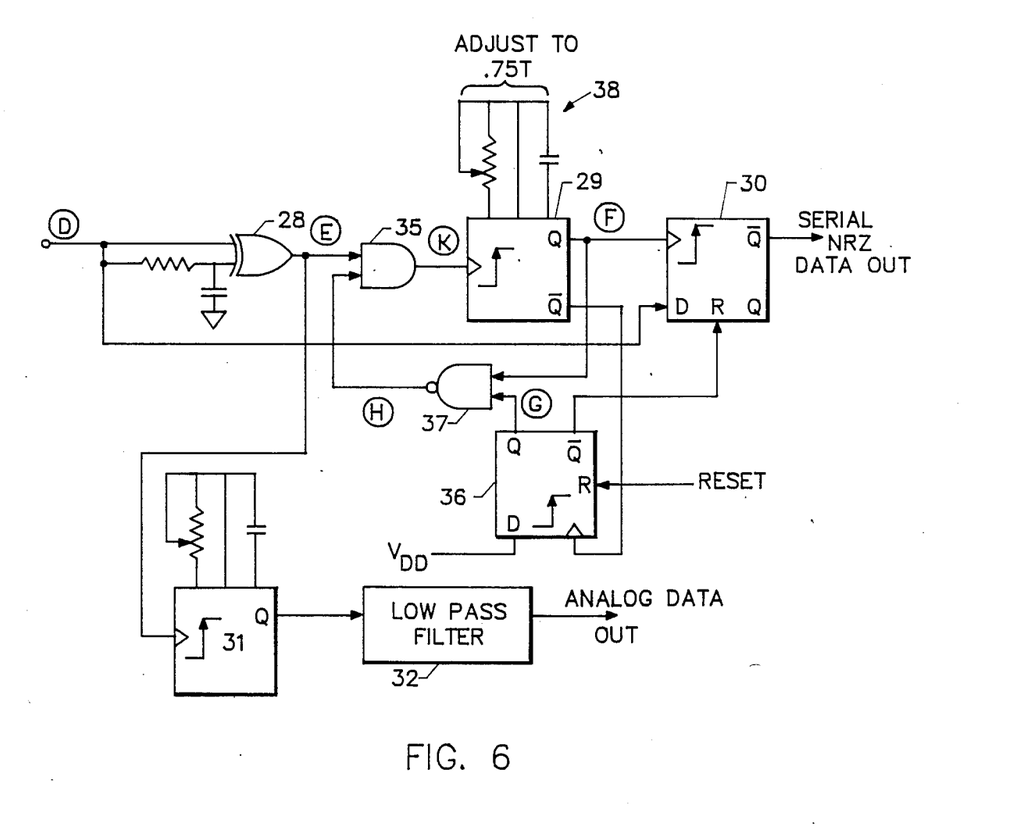
FIG. 6 is still another embodiment of the decoding and demodulating portion of the receiver.
Figure 7:
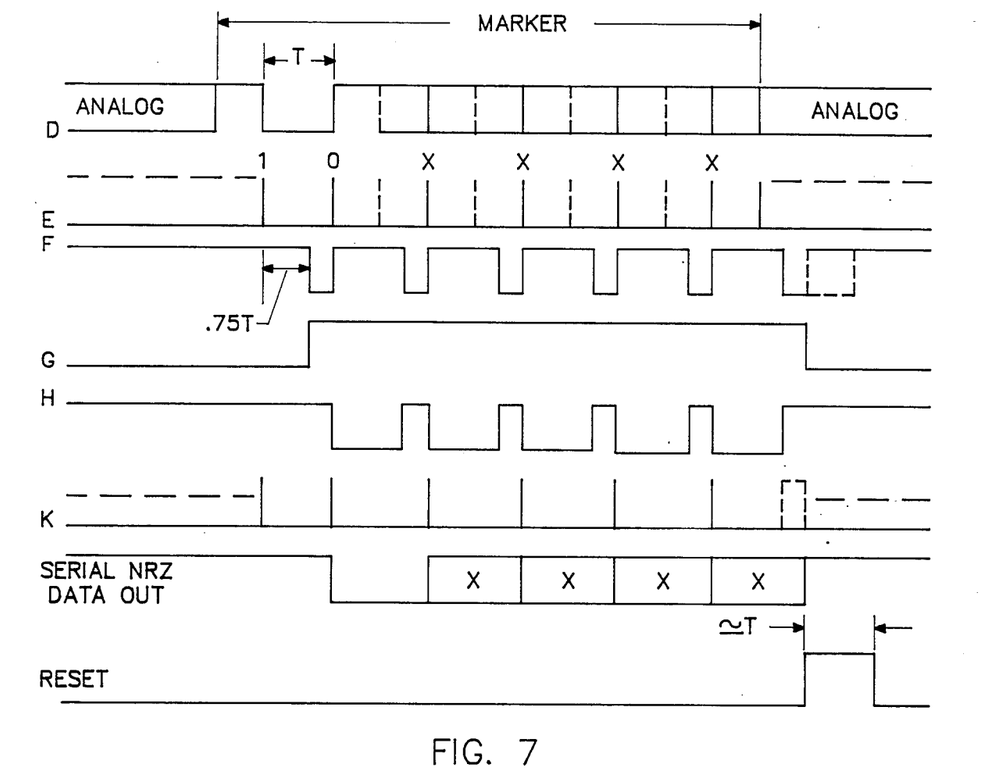
FIG. 7 is a composite diagram of signals which occur at given locations within the receiver in the third mode of operation using the embodiment illustrated in FIG. 6.

FIG. 6 illustrates an embodiment for obtaining the information from analog and digital transmitted signals in mode three. Using the waveforms in FIG. 7, it is seen that waveform CIRCLE D appears at the input of EXOR gate 28. And gate 35 sends its signal to one-shot multivibrator 29 (as in FIG. 5) which in turn provides an output to output flip flop 30. Reset flip flop 36 acts to reset the output flip flop 30 and enable clocking of the one-shot multivibrator 29 through AND gates 35 and 37. The R-C combination 38 is set to 0.75 T or a frequency of 1/1.5 T, where T is the bit duration. Referring to FIG. 7 it may be seen how a "marker" signal of four digital bits (sixteen possible combinations) may be sent within an analog signal.

In such combined mode, mode three, the range of the FM frequency includes the bit rate 1/T while transmitting in the digital mode (mode 1). The maximum frequency should be limited by the Q of the transmitter L-C circuit. The minimum frequency should be limited such that one-shot multivibrator 29 will always get set while receiving the incoming FM analog data.

In the fourth mode of operation, in FIG. 4, the switch 22 is set to A and switch 26 is set to D, and the output of the VCO 20 takes the place of the clock and causes the shifting in the shift register. The MUX will be switched by an input such that the VCO center frequency is maintained at 2048 Hz. This MUX input will have, in addition to a baseline necessary to maintain the 2048 Hz center frequency, a modulation which in turn will low-index FM modulate the VCO. If the modulation index of the VCO is low, the external device will be able to demodulate both the digital PSK signal and the analog FM signal, which are both being transmitted simultaneously and continuously.

FIG. 5 indicates a way in which the demodulation of such information might be obtained. In this mode four, (both digital and analog data being sent simultaneously) line connection 33 is utilized instead of line connection 34. This is because only the mid-bit transitions have to be counted; the inter-bit transitions may or may not be present depending upon the data. The FIG. 5 embodiment thus recovers both the digital and analog data.

FIG. 10 illustrates a binary slicer as shown at 16 in FIGS. 1 and 4. It is a common device which suddenly turns on as its input increases and then turns off when the input is lowered. It commonly is termed a Schmitt trigger, snap-action amplifier or a comparator with hysteresis because of its dead band. It is useful in squaring up analog signals.

Figure 11:
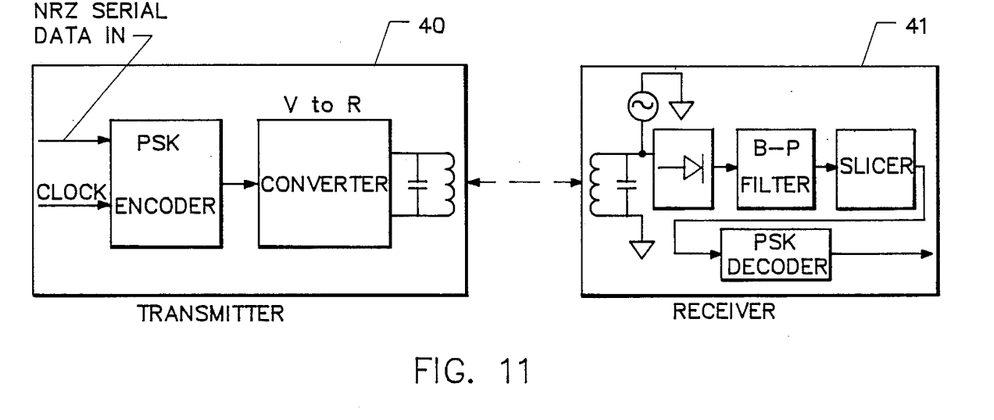
FIG. 11 is a block diagram showing the fundamental elements of one embodiment of the invention.

FIG. 11 illustrates the transmitter 40 and receiver 41 of the device of the invention. The transmitter, of course, may be inside the patient or outside and the receiver vice versa. There may be a transmitter and receiver inside and transmitter and receiver outside.

Figure 12:
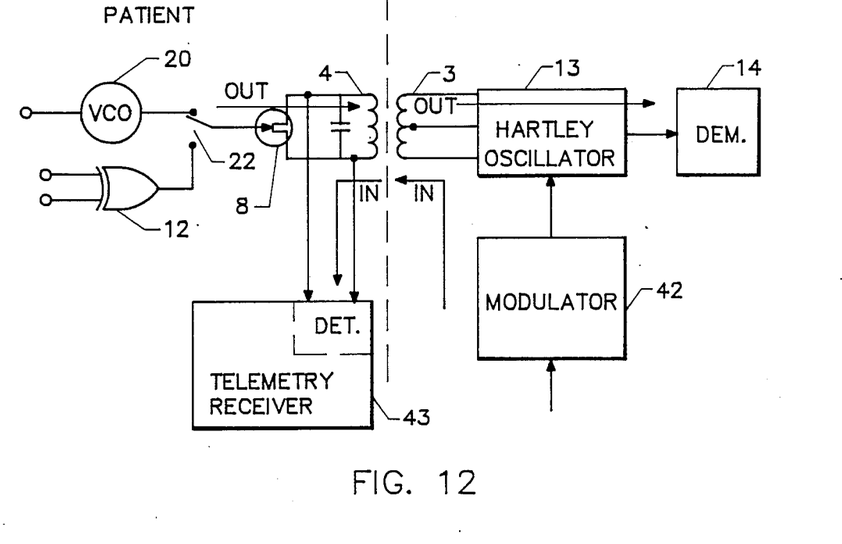
FIG. 12 is a schematic showing how information may be telemetered to the implanted device.

FIG. 12 illustrates summarily how transmitter and receiver components may be shared. A telemetry receiver 43 of an implanted device utilizes the same L-C circuit that the VCO 20 and the EXOR gate 12 utilize. The external unit, which is both a receiving unit and a programming, or transmitting unit, shows a Hartley oscillator 13, whic his used both in receiving and in transmitting. Other oscillators could, of course, be used. The demodulator or detector 14 receives the information obtained from the implanted device. The modulator 42 modulates the oscillator 13 for transmitting information into the implanted device. Inductive coil 4 receives such information which is detected in telemetry receiver 43.

FIG. 13 is an implementation of the invention using impulse-type coil driving. The EXOR gate 12 in FIG. 1 is replaced by an encoder 45 which will encode the data out of the shift register 10 in accordance with an encoding scheme such as those mentioned; namely, PSK, FM, MFM or MM. A switch 46 connects the capacitor 6 to the internal power source when the decoder output is zero, or across the coil 4 when this output is one. When connected to the power source the capacitor 6 charges to the power source, and when the switch 46 connects capacitor 6 across the coil, a damped oscillation is produced. This is received by external coil 3, AM demodulated, filtered and binary sliced by circuit elements 14, 15, and 16. The resulting binary data will enter a data decoder 17 which will recover the original NRZ data. In this method of operation, oscillator 13 need not furnish the driving power for coils 3 and 4 and, therefore, switch 47 is provided in order to disconnect oscillator 13 from the circuit.

Coil 4 and capacitor 6 may still be used as a receiving circuit for a receiver 43 as discussed in connection with FIG. 12. Switch 46 would be held in the downward position (so as to hold coil 4 and capacitor 6 in parallel with each other) during such manner of operation.

For the case in which the data encoder 45, FIG. 13, is a PSK encoder (using an EXOR gate 12 as in FIG. 1), the signals generated are as shown in FIG. 14. It can be shown that the pulse train C in FIG. 14 represents a MFM encoding. The same is true for received signal D. In such case, data decoder 17 must convert from MFM to NRZ data. The schematic for such decoder and other possible decoders for bi-phase, Miller, or other PCM schemes, are not shown inasmuch as such decoders are of a large variety and are well-known to those skilled in the art. Numerous publications disclose various encoding and decoding schemes. Reference is made to an article by Richard H. Severt in "Computer Design", May 1980, page 181 et seq., and "Telecommunications Engineering", Lindsey and Simon, Prentice-Hall, 1973, p. 11.

Figure 15:
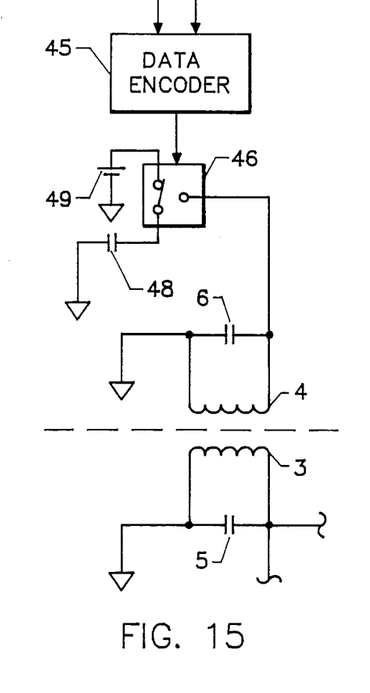
FIG. 15 is an alternate manner of charging capacitor 6 of FIG. 13.

FIG. 15 shows a slightly different manner of charging L-C combination 4 and 6. Switch 46 connects capacitor 48 so as to be charged by battery 49 and then connects capacitor 48 to charge capacitor 6. Both capacitors are then connected across coil 4. This configuration may be useful when the transmitting frequency is different from the receiving frequency.

Figure 16:
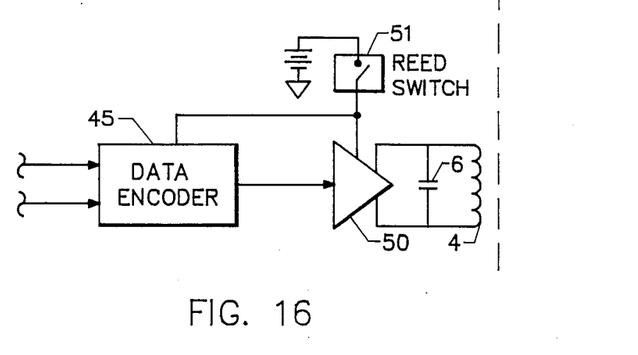
FIG. 16 shows an active rf transmitter in the implanted device.

FIG. 16 illustrates the use of an active rf transmitter within the implanted device. An amplifier 50, when energized by reed switch 51 (which may be done by an external magnet as is commonly known in the art) transmits through the use of coil 4 to a receiver outside the patient's body. The signals transmitted are those received from the encoder 45.

Figure 17:
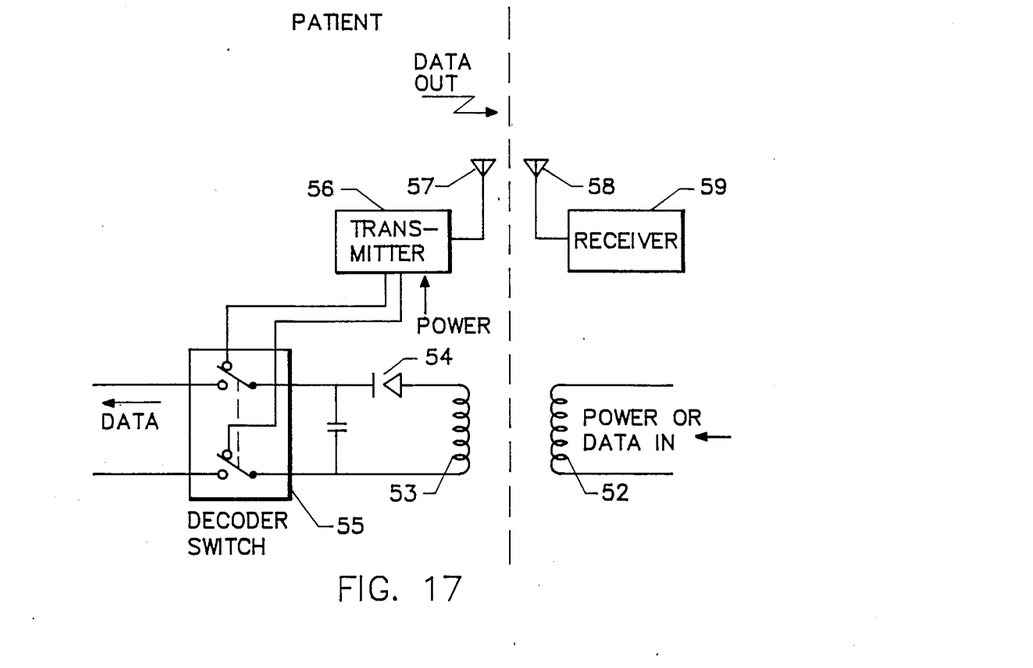
FIG. 17 illustrates power or data transmission into an implanted device at one frequency and data transmission out of the implanted at another frequency.

It is to be understood that various known transmission techniques may be utilized. At the very high frequencies, (VHF), the involved battery drain may be unacceptable. One method of obtaining adequate energy to transmit would be to feed electrical energy into the implanted device at one frequency and receive data out at another frequency. FIG. 17 illustrates such a scheme, showing an input coil 52 (providing power or data, or both). Coil 53, which is part of the implanted device, receives the energy or the data, and by means of diode 54 rectifies or demodulates it. A decoder switch 55 may be used to determine the routing within the implanted device. Such decoder switch may be set by a reed switch (from an external magnet) or by the initial transmission, which may be encoded to identify where the subsequent transmission is to be sent. If energy is being provided, it is used to energize transmitter 56 which may transmit out on a different frequency, any data to be provided by the implanted device. Antenna 57, which may be an antenna or a coil, transmits the energy to be picked up by the outside antenna, or coil, 58 which is connected to receiver 49. The use of ferrite coils, ferrite sticks, or ferrite beads could be used to facilitate the transfer of power to the implanted device. Of course, energy may simply be furnished to charge an implanted battery as taught in U.S. Pat. No. 3,942,535, for Rechargeable Tissue Stimulating System, invented by Joseph H. Schulman, issued Mar. 9, 1976, which, in turn, may be used to provide power for the transmission of data. Such availability of energy within the implanted device (either from battery or external source)

would allow going to much higher frequencies despite the added power losses. It is also possible using the concept shown in FIG. 17 and other known methods, to send data in, while data is being received out. Thus, communication by the implanted device with the outside, could be in full duplex. This could also be accomplished by a separate transmission and reception system in the implanted system as well as in the outside system.

As is commonly known in the data transmission art, the data might well be encoded for error checking and error correcting, (e.g., using redundancy, parity checking, Hamming or other codes,) and also, the system may use handshaking and other digital data transfer techniques well-known to those skilled in the digital data art and the communications art.

Although the invention has been described and illustrated in detail, it is to be clearly understood that the same is by way of illustration and example only and is not to be taken by way of limitation, the spirit and scope of this invention being limited only by the terms of the appended claims.

I claim:

1. A system for simultaneously transmitting digital and analog information from an implanted device to an external device, said system comprising:
    frequency modulation means within said implanted device for generating a carrier signal and frequency modulating said carrier signal with analog information;
    shift register means within said implanted device for holding digital data, said shift register means including means for serially clocking the digital data out of said shift register means in response to a clock signal;
    means for applying said frequency modulated carrier signal from said frequency modulation means to said shift register means, said frequency modulated carrier signal comprising the clock signal that is used to serially clock the digital data out of said shift register means; and
    transmitting means within said implanted device for serially transmitting to said external device the digital data clocked out of said shift register means by said frequency modulated carrier signal, whereby both said digital data and the analog information, used to modulate said frequency modulated carrier signal, are contained in the signal transmitted by said transmitting means.

2. The analog and digital transmitting system of claim 1 wherein said frequency modulation means includes means for modulating said carrier signal with analog information from a plurality of sources.

3. The analog and digital transmitting system of claim 1 wherein said serial transmitting means includes digital modulation means for modulating the digital data clocked out of said shift register means between two possible data representations as a function of whether the digital data comprises a digital one or a digital zero.

4. The analog and digital transmitting system of claim 3 wherein said digital modulation means comprises a phase shift keyed (PSK) modulation device that shifts the phase of the digital data clocked out of said shift register means between two phase values as a function of whether the digital data comprises a digital one or a digital zero.

5. The analog and digital transmitting system of claim 4 wherein said PSK modulating device comprises an Exclusive-Or gate having the digital data clocked out of said shift register means applied to a first input terminal thereof and having the frequency modulated carrier signal, used to clock the digital data out of said shift register means, applied to a second input terminal thereof.

6. The analog and digital transmitting system of claim 1 wherein said external device comprises:
    receiving means for receiving the data serially transmitted out of said implanted device by said transmitting means; and
    demodulating means for recovering said digital data and said analog information from said received data.

7. The analog and digital transmitting system of claim 6 wherein said demodulating means comprises:
    a digital decoder for recovering the digital data contained within the data received by said receiving means;
    an FM demodulator for extracting an FM signal from the data received by said receiving means, said FM signal being representative of the frequency modulated carrier signal generated by the frequency modulation means of said implanted device; and
    means for recovering said analog information from said FM signal.

8. An implantable transmitting unit for selectively transmitting digital or analog data from an implantable medical device, said transmitting unit comprising:
    carrier signal generation means for generating a carrier signal;
    analog modulating means for modulating said carrier signal with analog data;
    shift register means for holding digital data;
    clocking means for serially shifting said digital data through said shift register means in response to a clock signal;
    exclusive-or gate means for receiving said clock signal and the data clocked out of said shift register means by said clocking means, and for generating a modulated signal that represents a phase shift keyed (PSK) signal of said digital data;
    switch means for selecting one or the other of said modulated carrier signal or said PSK signal for transmission; and
    transmitting means for transmitting the signal selected by said switch means.

9. The transmitting unit of claim 8 wherein said analog modulating means comprises frequency modulation (FM) means for frequency modulating said carrier signal as a function of said analog data.

10. The transmitting unit of claim 9 wherein said clocking means comprises means for applying said FM carrier signal to said shift register means as said clock signal, and wherein said FM carrier signal is further applied to said exclusive-or gate means as said clock signal.

* * * * *